United States Patent [19]

Nunokawa

[11] Patent Number: 4,712,894
[45] Date of Patent: Dec. 15, 1987

[54] OPHTHALMOSCOPIC INSTRUMENT HAVING WORKING POSITION DETECTING MEANS

[75] Inventor: Kazuo Nunokawa, Tokyo, Japan

[73] Assignee: Tokyo Kogaku Kikai Kabushiki Kaisha, Tokyo, Japan

[21] Appl. No.: 473,454

[22] Filed: Mar. 10, 1983

Related U.S. Application Data

[63] Continuation-in-part of Ser. No. 304,575, Sep. 22, 1981, Pat. No. 4,511,227.

[30] Foreign Application Priority Data

Mar. 15, 1982 [JP] Japan ............................ 57-40405

[51] Int. Cl.[4] .................................... A61B 3/14
[52] U.S. Cl. .............................. 351/208; 351/211
[58] Field of Search ............................ 351/208, 211

[56] References Cited

U.S. PATENT DOCUMENTS 4,257,688 3/1981 Matsumura .
4,283,124 8/1981 Matsumura ................... 351/211

Primary Examiner—Rodney B. Bovernick
Assistant Examiner—P. M. Dzierzynski
Attorney, Agent, or Firm—Brumbaugh, Graves, Donohue & Raymond

[57] ABSTRACT

Ophthalmoscopic instrument having working position detector. An object lens has an optical axis and is adapted to be positioned to confront a patient's eye at a working distance. The patient's cornea has a center of curvature. An observing optical system focuses a light beam reflected from the eye and passing through an objective lens on an image plane. A detecting system detects that the eye is properly positioned with respect to the objective lens. The detecting system includes at least two apertures allowing light beams from a single target mark to pass therethrough. A target mark projection system projects the beams passed through the respective apertures in directions crossing each other on the optical axis of the objective lens so that a target mark image is formed at the center of curvature of the cornea when the eye is properly positioned with respect to the objective lens. A target mark image plane forms a target mark image by mirror reflection from the cornea of the light beams projected through the target mark projection system when the patient's eye is properly positioned, and a target mark image observation system provides observation of the target mark image on the target mark image plane in superposition with a reference mark.

5 Claims, 14 Drawing Figures

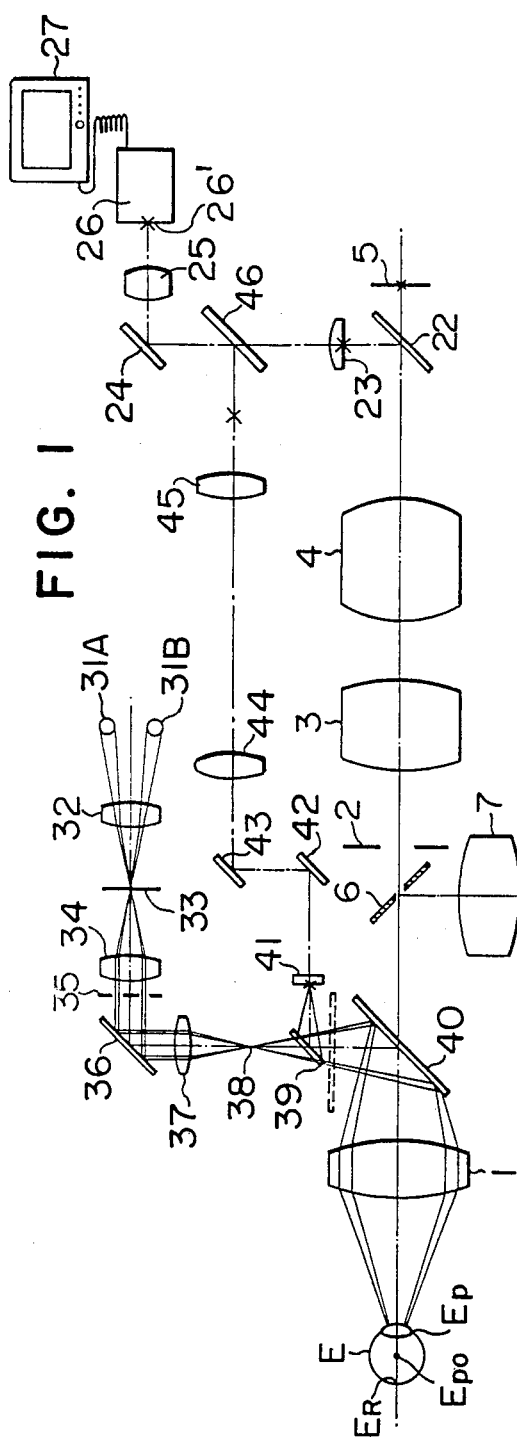

FIG. 5A
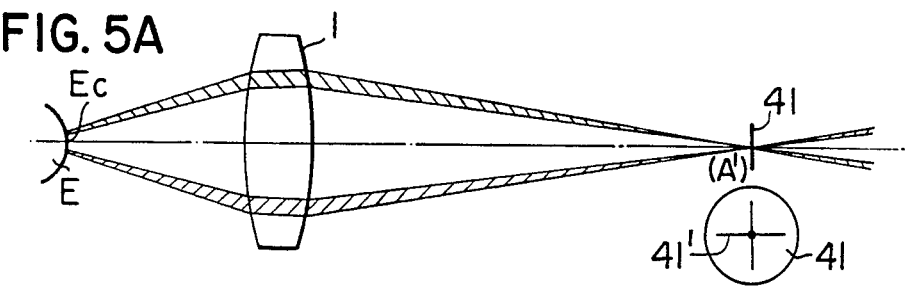
FIG. 5A'
FIG. 5B
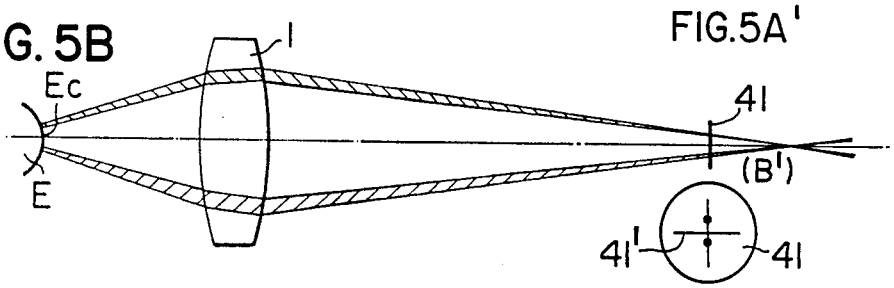
FIG. 5B'
FIG. 5C
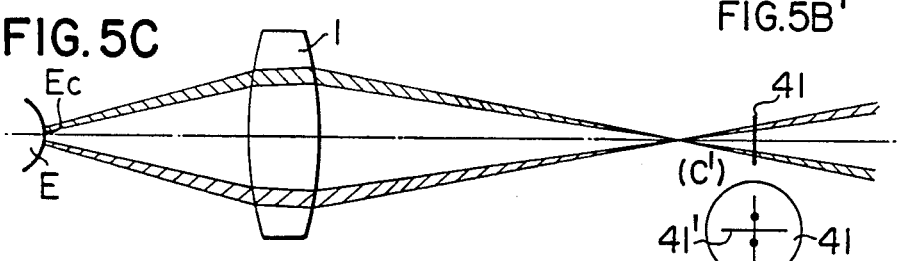
FIG. 5C'
FIG. 5D
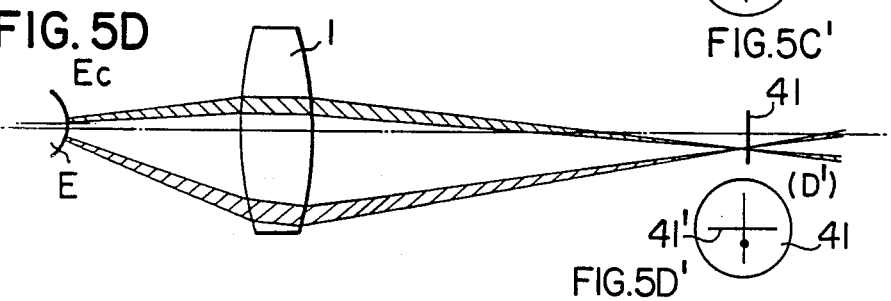
FIG. 5D'
FIG. 6
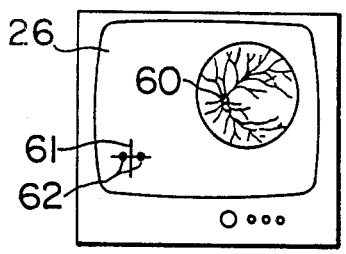
FIG. 7
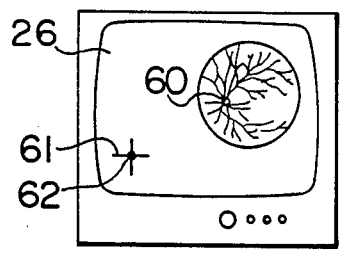

OPHTHALMOSCOPIC INSTRUMENT HAVING WORKING POSITION DETECTING MEANS

This is a continuation-in-part of U.S. application Ser. No. 304,575, filed Sept. 22, 1981, now U.S. Pat. No. 4,511,227 issued 4-16-1985.

BACKGROUND OF THE INVENTION

This invention relates to an ophthalmoscopic instrument equipped with means for detecting that the patient's eye is properly positioned with respect to the instrument.

In an ophthalmoscopic instrument, it is required that the instrument be positioned at a proper relationship with respect to the patient's eye. More specifically, it is necessary to make the optical axis of the instrument aligned with that of the patient's eye to establish an optical axis alignment, and to position the instrument at a predetermined distance from the patent's eye to establish a proper working distance adjustment. If the alignment and the working distance adjustment are not satisfactory in an eye fundus camera, for example, a part of the light projected to the patient's eye and reflected at the cornea is allowed to pass into the optical path of the instrument causing flaring and ghosting. Also, if the optical axes alignment and the working distance adjustment are imperfect in a refractometer, measurement errors will occur. A variety of devices have therefore been proposed for detecting the proper positional relationship between the patient's eye and the ophthalmoscopic instrument in the past.

As an example of the conventional devices for detecting the proper position for the eye being examined, an eye fundus camera is provided with an optical system by which a target mark is projected onto the cornea of the eye being examined, and the proper position of the eye is detected from the position and focusing of the image of the target mark reflected from the corneal surface of the eye. In the target mark projecting system of this type, however, the target mark projecting light beam is projected through a very small aperture so that the depth of focus is increased, and hence it is difficult to judge the focus of the projected target mark image accurately for the purpose of detecting the proper position of the eye being examined.

BRIEF SUMMARY OF THE INVENTION

It is an object of this invention to provide an ophthalmoscopic instrument equipped with means for detecting the proper position of the eye being examined so that the above problem in the prior art can be readily solved.

Another object of this invention is to provide an ophthalmoscopic instrument equipped with means for easily detecting the proper position of the eye being examined.

To achieve the above and other objects, the ophthalmoscopic instrument according to this invention is composed of objective lens means having an optical axis and adapted to be positioned to confront a patient's eye at a working distance, said patient's eye having a cornea with a center of curvature, an observing optical system adapted to focus a light beam reflected from the eye and passing through the objective lens means on an image plane, means for detecting that the eye is properly positioned with respect to the objective lens means, said detecting means including at least two apertures allowing light beams from a single target mark to pass therethrough, a target mark projection system adapted to project at least two light beams passed through the respective apertures in directions crossing each other on the optical axis of the objective lens so that a target mark image is formed at the center of curvature of the cornea of the eye when the eye is properly positioned with respect to the objective lens means, a target mark image plane for forming a target mark image by mirror reflection at the cornea of the light beams projected through the target mark projection system when the patient's eye is properly positioned, a target mark image observation system for observing the target mark image on the target mark image plane in superposition with a reference mark.

The above and other objects of the present invention will become apparent from the following descriptions of a preferred embodiment taking reference to the accompanying drawings, in which;

BRIEF DESCRIPTION OF THE DRAWINGS

FIG. 1 is a diagrammatical illustration of an optical system of an eye fundus camera embodying the features of the present invention;

FIG. 2 is a view showing an example of the target mark used in the target projection system;

FIG. 3 is a view showing an example of the aperture plate in the target projection system;

FIG. 4 is a view showing the diffusion plate for forming a target mark image;

FIGS. 5(A), (B), (C) and (D) diagramatic illustrations show the principle of detection of the patient's eye in accordance with the present invention; and FIGS. 5(A)' to 5(D)' are views showing the target mark and projected images corresponding to the eye locations of FIGS. 5(A) to 5(D), respectively.

FIGS. 6 and 7 show a monitor TV on which the target mark image is produced in accordance with the present invention.

DESCRIPTION OF PREFERRED EMBODIMENTS

Referring to the drawings, particularly to FIG. 1, there is shown an optical system of an eye fundus camera including a photographic optical system composed of an objective lens 1 disposed so as to face an eye being examined E, an aperture 2 disposed in substantially conjugate with the pupil Ep of the eye relative to the objective lens 1, a focusing lens 3, an imaging lens 4, and a photographing film 5. An eye fundus observation system is composed of an inclined reflecting mirror 22 disposed in front of the film 5, a field lens 23 disposed in the optical path of the reflection from the reflecting mirror 22, a reflection mirror 24, a relay imaging lens 25, an infrared camera tube 26, and a monitor TV 27. A photoelectric surface 26' of the infrared camera tube 26 is disposed in conjugate with the film 5.

An illuminating optical system is composed of an inclined apertured mirror 6 located in the optical path of the photographic optical system at a position in front of the aperture 2, a relay lens 7 disposed in the optical path of the reflection from the perforated mirror 6, a condensing lens 9, an annular slit 10, a tungsten lamp 11, an infrared filter 12 allowing only infrared rays to pass therethrough, two condensing lenses 13, a half mirror 14, and a xenon lamp 15 serving as a photographing light source. The illuminating light emitted from the two lamps 11 and 15 strike the reflecting surface of the perforated mirror 6 in the form of a ring and is reflected so as to pass through the objective lens 1 and then illuminate the eye fundus $E_R$.

With the arrangement described above, when observing the fundus of the eye being examined, the eye fundus is illuminated by infrared rays from the tungsten lamp 11 which passes through the infrared filter 12. The infrared image of the eye fundus is subject to photoelectric conversion in the camera tube 26 and is then displayed on the screen of the monitor TV 27 as a visible image. When photographing the fundus of the eye, the eye is illuminated by the light from the xenon lamp 15 and an image of the eye fundus is recorded on the surface of the film 5.

The instrument includes a device for detecting the proper position of the eye being examined. This detection device comprises a target mark projection system for projecting a target mark onto the eye being examined, and a target mark image observation system adapted to form and observe target mark images reflected by the cornea from the light reflected by the surface of the cornea of the eye being examined. The target mark projection system includes a pair of infrared light sources 31a and 31b symmetrically positioned with respect to the optical axis. The light beams from the light sources 31a and 31b are condensed through a condenser lens 32 so as to illuminate a target mark 33 from two different directions. As shown in FIG. 2, the target mark 33 is formed of an aperture 33' which is a single pin hole. The light from the target mark 33, that is, the light which has passed the pin hole aperture 33' goes through a first relay lens 34 is then divided into two thinner light beams through a two-hole aperture plate 35 having a pair of elongated holes 35', as shown in FIG. 3. The two beams divided in this way are first imaged at a point 38 after passing through a reflecting mirror 36 and a second relay lens 37, and are then projected toward the eye being examined E through a half mirror 39, another retractable half mirror 40 and the objective lens 1. When the eye being examined is in the proper position, images of the target mark 33 are formed at the center of curvature Epo of the cornea of the eye being examined. This means that the light beams from the aperture plate 35 are projected through the objective lens 1 so that they intersect each other on the optical axis of the objective lens 1 at the center of curvature Epo of the eye cornea. When the eye being examined is in the proper position, the light beams projected through the above target mark projection system are reflected normally by the surface of the cornea of the eye E and returned back along the same optical path as that of the projected light beams.

The target mark image is so constituted that the light beams reflected by the cornea of the eye are passed through the objective lens 1 and the two half mirrors 40, 39 to be projected to a diffusion plate 41 to form an image of the target mark. The diffusion plate 41 has a cross-shaped reference mark 41' thereon, as shown in FIG. 4, and it is disposed in conjugate with the target mark 33. Since the light beams from the aperture plate 35 are projected so that they intersect each other on the optical axis of the objective lens 1 at the center of curvature Epo of the eye cornea when the eye is in the proper position, the target mark image is formed on the diffusion plate 41 by a mirror reflection at the cornea surface of the projected light beams.

An image of the diffusion plate 41 on which are projected the target mark images reflected by the cornea is relayed through the reflecting mirrors 42 and 43, relay lenses 44 and 45, a half mirror 46, a reflecting mirror 24 and a relay imaging lens 25, and are then focused onto the photoelectric surface 26' of the camera tube 26. The photoelectric surface 26' is disposed in conjugate with the diffusion plate 41. As a result, an image of the cross-shaped reference mark 41' on the diffusion plate 41 and the target mark image are both formed on the photoelectric surface 26' in a superimposed relationship. These infrared images projected onto the photoelectric surface 26' are converted into an electric signal by the camera tube 26 and then displayed on the screen of the monitor TV 27 as a visible image. As previously noted, in this embodiment the diffusion plate is disposed at the position at which the target mark image is formed by a mirror reflection at the cornea of the target mark projection. This leads to the effect that the aperture of the relay lenses used for relaying these images onto the photoelectric surface 26' of the camera tube 26 can be reduced.

The principle of detecting the proper position for the eye being examined in the thus arranged device will be explained hereinafter. FIG. 5 shows various ways in which light beams reflected by the cornea Ec of the eye E are imaged onto the diffusion plate 41 through the objective lens 1.

(1) When the eye is in the proper position, i.e., when both optical axis alignment and the working distance adjustment are perfect, the light beams reflected at the cornea pass along the same optical path as that of the projected light beams and a target mark image is formed by a mirror reflection at the cornea surface at the center of the cross-shaped reference mark 41' on the diffusion plate 41 as a single target mark image, as shown by A' in FIG. 5A.

(2) When the optical axis alignment is established but the working distance is too short, the target mark image is focused behind the diffusion plate 41, as shown in FIG. 5B. Thus, two images are formed on the diffusion plate 41 and these two images are separated from each other in vertical direction, as shown by B' in FIG. 5B.

(3) When the optical axis alignment is established but the working distance is too long, the target mark images are focused in front of the diffusion plate 41, as shown in FIG. 5C, so that there are formed on the diffusion plate 41 two target mark images separated from each other in the vertical direction, similar to the case of (2), as indicated by C' in FIG. 5C.

(4) When the working distance adjustment is satisfactory but the optical axis alignment is incorrect, i.e., when the center of curvature Epo of the cornea of the eye Ec is not on the optical axis of the objective lens 1, a single target image is formed on the diffusion plate 41 at a position away from the center of the reference cross-shaped target mark 41', as indicated by D' in FIG. 5D.

(5) When both the operating distance adjustment and the optical axis alignment are incorrect, the above shift of the target mark images on the diffusion plate 41 are combined.

These various target mark images on the diffusion plate 41 can be observed on the screen of the monitor TV 27, as previously stated.

In the arrangement described above, when the tungsten lamp 11 and the infrared light sources 31A, 31B are lit, an eye fundus image 60 is displayed roughly at the center on the screen of the monitor TV 27, as illustrated in FIG. 6, and an image 61 of the cross-shaped reference mark 41' and the target mark images 62 corresponding to the two infrared light sources 31A, 31B are displayed together in the bottom left-hand corner of the screen in a superimposed relationship. The relative positional relationship of the fundus camera and the eye being examined is then varied so that the two target mark images 62 coincide with each other to form a single target mark image which is also located at the center of the reference cross-shaped target mark image 61, as shown in FIG. 7. With this, the proper position adjustment of the eye being examined is completed.

Although infrared light sources are used in the above device for detecting the proper position of the eye being examined, visible light sources may be used instead to make it possible to observe the target mark images directly through a finder. The reference target mark is formed on the diffusion plate 41 in this embodiment, but the reference target mark image could also be displayed directly on the screen of the monitor TV using picture signals. Furthermore, the target mark images could be displayed superimposed over the eyeground image on the screen of the monitor TV 27.

The half mirror 40 is disposed at a position indicated by solid lines in FIG. 1 during the proper position adjustment for the eye being examined, for the purpose of observing the eyeground image. But during photographing the half mirror 40 springs up to a position indicated by broken lines in order to effectively utilize the photographing light and protect the photoelectric surface 26' of the camera tube 26.

Since this invention is constituted as stated above, the proper position of the eye can be detected easily. In other words, if the operating distance, that is, the spacing between the ophthalmoscopic instrument and the eye being examined becomes inappropriate, there are formed separated target images. Thus, the proper working distance can be detected with ease, and this detection can be performed with a much higher accuracy when comparing with the prior art device in which the detection is made by observing a focusing condition. Further, it is also possible to know the amount of offset from the proper position by the spacing between two target mark images.

On the other hand, the error in the optical axis alignment appears in the form of a movement of the single superimposed target mark image, or the center of the two separated target mark images, from the reference mark. Thus, the alignment of the optical axes can be done perfectly by making the single surperimposed target mark image, or the center of the two separated target mark images, coincide with the reference target mark. It is a matter of course that the optical axis alignment can be performed independently of the working distance adjustment.

The invention has thus been shown and described with reference to a specific embodiment, however, it should be noted that the invention is in no way limited to the details of the illustrated arrangements but changes and modifications may be made without departing from the scope of the appended claims.

I claim:

1. An ophthalmoscopic instrument comprising objective lens means having an optical axis and adapted to be positioned to confront a patient's eye at a working distance, said patient's eye having a cornea with a center of curvature, an observing optical system adapted to focus a light beam reflected from the eye and passing through the objective lens means on an image plane, means for detecting that the eye is properly positioned with respect to the objective lens means, said detecting means including a single target mark, a target mark image projection system adapted to project said target mark image by way of at least two light beams crossing each other on the optical axis of the objective lens means so that a target image is formed by each of the beams at the center of curvature of the cornea of the eye when the eye is properly positioned with respect to the objective lens means, a target mark image plane wherein target mark images are formed by mirror reflection, at the cornea, of the light beams projected through the target mark projection system when the patient's eye is properly positioned, a target mark image observation system for observing the target mark images on the target mark image plan in superposition with a reference mark, whereby said target mark images on the target mark image plane are formed in superposition with said reference mark at predetermined positions when the eye is properly positioned with respect to the objective lens means.

2. An instrument in accordance with claim 1 in which said detecting means includes reflecting means for reflecting at least a part of the light beams with have been reflected at the cornea surface and have passed through the objective lens means to a diffusion plate defining said target mark image plane, said target mark image observation system including optical relay means for relaying light beams from said diffusion plate.

3. An instrument in accordance with claim 2 in which said reference mark is provided on said diffusion plate.

4. An instrument in accordance with claim 2 in which said target mark image observation system includes an image taking tube having a photoelectric surface located so that a target mark image is formed thereon by said optical relay means, a monitoring TV for producing a visible image based on electric signals from said image taking tube.

5. An eye fundus camera including objective lens means having an optical axis and adapted to be placed in front of a patient's eye with a working distance therebetween; an illuminating optical system having illuminating light source means, a ring-shaped aperture substantially conjugate with a pupil of said patient's eye with respect to the objective lens means and a ring-shaped reflector having a central aperture and disposed on the optical axis of said objective lens means in substantially conjugate relationship with the pupil of the patient's eye; an observing optical system having an image plane for producing an image of fundus of the patient's eye; means for detecting that the eye is properly positioned with respect to the objective lens means, said detecting means including at least two apertures allowing light beams from a single target mark to pass therethrough, a target mark projection system adapted to project at least two light beams passed through the respective apertures in directions crossing each other on the optical axis of the objective lens so that a target mark image is formed at the center of curvature of the cornea of the eye when the eye is properly positioned with respect to the objective lens means, a target mark image plane located in conjugate with the center of curvature of the cornea of said eye for forming a target mark image by mirror reflection at the cornea of the light beams projected through the target mark projection system when the patient's eye is properly positioned, a target mark image observation system for observing the target mark image on the target mark image plane in superposition with a reference mark.

* * * * *